United States Patent [19]
Bergkuist et al.

[11] Patent Number: 5,158,868
[45] Date of Patent: Oct. 27, 1992

[54] METHOD OF SAMPLE ANALYSIS

[75] Inventors: Carolyn Bergkuist, Hampstead, N.H.; Yvonne Fraticelli, Newton; Theodore S. Geiselman, Groveland, both of Mass.

[73] Assignee: Iniziative Marittime 1991, s.r.l, Turin, Italy

[21] Appl. No.: 597,070

[22] Filed: Oct. 15, 1990

Related U.S. Application Data

[62] Division of Ser. No. 74,882, Jul. 17, 1987, Pat. No. 4,997,627.

[51] Int. Cl.[5] .................... C12Q 1/00; C12Q 1/58; C12Q 1/26
[52] U.S. Cl. ............................ 435/4; 435/12; 435/25; 435/180; 436/52; 436/68; 436/108; 436/111
[58] Field of Search ............. 435/4, 12, 25, 180; 436/52, 68, 108, 111, 518

[56] References Cited

U.S. PATENT DOCUMENTS

| | | | |
|---|---|---|---|
| 3,915,804 | 10/1975 | Messing | 435/12 |
| 3,926,734 | 12/1975 | Gray | 435/12 |
| 4,153,513 | 5/1979 | Edelmann | 435/14 |
| 4,197,369 | 4/1980 | Weaver | 435/12 |
| 4,263,406 | 4/1981 | Bostick | 435/291 |
| 4,277,560 | 7/1981 | Gray | 435/7.93 |
| 4,420,564 | 12/1983 | Tsuji | 435/288 |
| 4,443,407 | 4/1984 | Weinberg | 422/82.04 |
| 4,476,005 | 10/1984 | Tokinaga | 204/403 |
| 4,490,235 | 12/1984 | Calzi | 204/409 |
| 4,525,265 | 6/1985 | Abe | 204/403 |
| 4,640,821 | 2/1987 | Mody | 422/81 |
| 4,759,828 | 7/1988 | Young | 204/153.12 |

FOREIGN PATENT DOCUMENTS 0101236 8/1983 European Pat. Off. .
58-209996 12/1983 Japan .

OTHER PUBLICATIONS

Laskin, *Enzymes & Immobilized Cells in Biotechnology*; 1985 pp. 7-8.
Leon, Luis P. "Continuous-Flow Analysis for Glucose in Serum, with Use of Hexokinase and Glucose-6--Phosphate Dehydrogenase Co-immobilized in Tubular Form", Clin. Chem. 26/1, 123-129 (1980).
Pacakova, Vera "Use of the Clark Oxygen Sensor With Immobilized Enzymes For Determination in Flow Systems", Analytical Chimica Acta, 159 (1984) 71-79.
Analytical Chemistry, vol. 55, No. 11, Sep. 1983, Columbus US pp. 1040-1053; J. Ruzicka: "Flow Injection Analysis, From Test Tube to Integrated Microconduits".

*Primary Examiner*—Robert J. Warden
*Assistant Examiner*—T. A. Trembley
*Attorney, Agent, or Firm*—Fish & Richardson

[57] ABSTRACT

A system for analyzing a biological fluid or the like for a constituent of interest comprises structure defining a sample inlet port, structure defining an analysis region, a measuring system connected in sensing relation to the analysis region, and structure defining a reaction chamber that has an immobilized enzyme capable of modifying the constituent of interest. Control means operates liquid flow means in a unidirectional sample flow mode to initially flow a sample of material to be analyzed from the sample inlet port to the reaction chamber and to the analysis region for a measurement of unmodified sample material, and then operates the liquid flow means in a bidirectional sample flow mode to oscillate the sample material in the reaction chamber and facilitate modification by the immobilized enzyme of the constituent of material in the sample. Modified sample material is then introduced into the analysis region and the measuring system is operated to obtain a measurement of modified sample material, the measurements of modified and unmodified sample material then being used to provide an indication of the amount of the constituent of interest in the sample material.

15 Claims, 1 Drawing Sheet

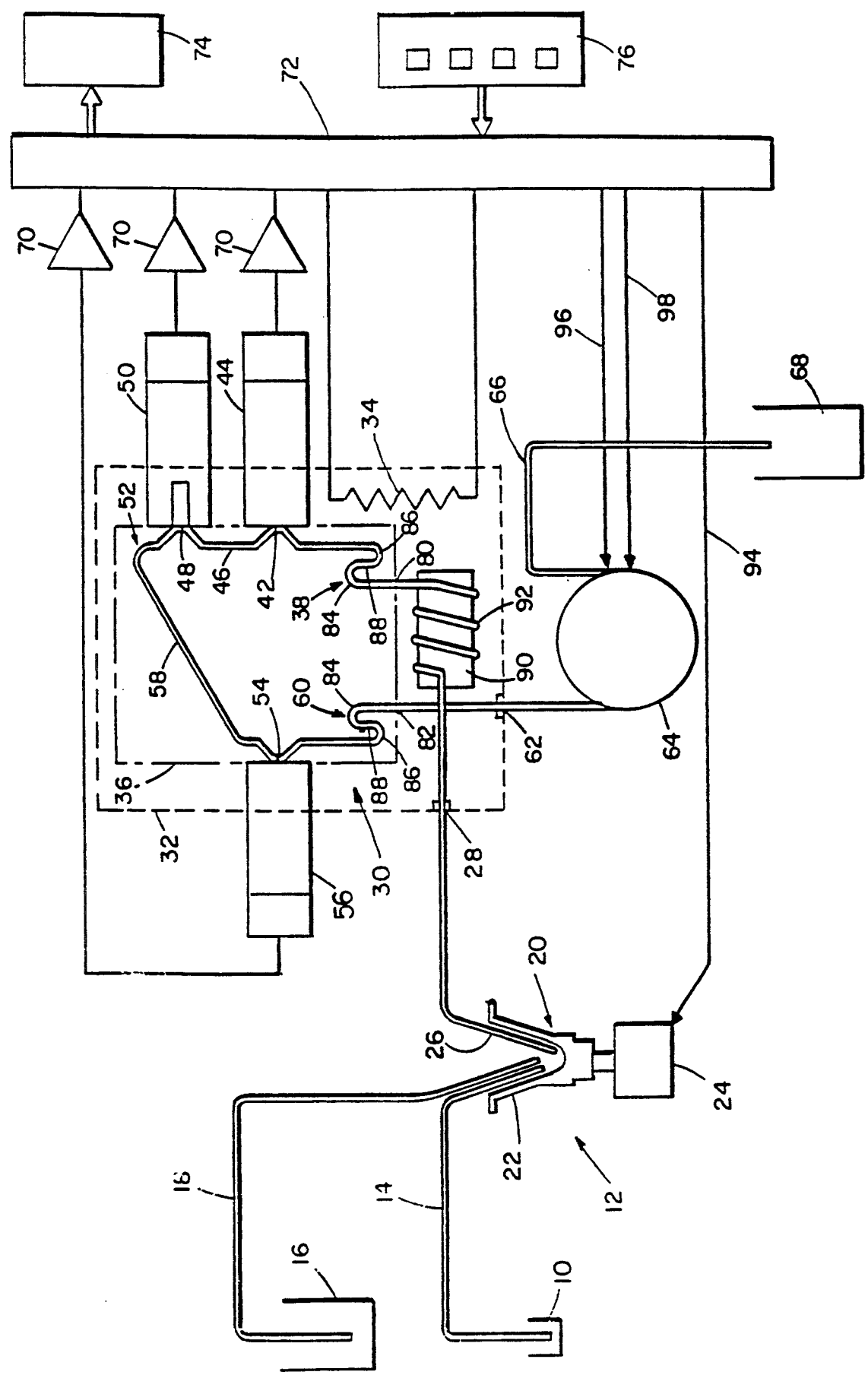

METHOD OF SAMPLE ANALYSIS

This is a divisional of application Ser. No. 07/074,882 filed Jul. 17, 1987.

This invention relates to methods and apparatus for the analysis of fluid samples and has particular application to methods and apparatus for analysis of parameters of biological fluids such as blood.

Accurate measurement of one or more constituents of a sample of biological fluid (whole blood, plasma, serum, urine, etc.) provides useful information for diagnosis, assistance in the control of life support devices, evaluation of the effectiveness of therapeutic measures, and the like. Various electrodes including polarographic electrodes and ion selective electrodes have been used in such constituent measurements. An immobilized enzyme has also been used to convert a constituent of interest in the sample to an ion detectable by the electrode, for example, urea may be enzymatically converted to ammonium ions which are detectable by an ammonium electrode. One problem with such measurements, however, is that another constituent, such as an interfering ion, present in the sample may contribute to the total output from the electrode, resulting in an erroneous indication of the amount of the constituent of interest present in the sample.

In accordance with one aspect of the invention, there is provided a system for analyzing a biological fluid or the like for a constituent of interest that comprises structure defining a sample inlet port, structure defining an analysis region, a measuring system connected in sensing relation to the analysis region, and structure defining a reaction chamber with immobilized enzyme in the reaction chamber that is capable of converting the constituent of interest to a constituent detectable by the measuring system. Control means operates liquid flow means in a unidirectional sample flow mode to initially flow a sample of material to be analyzed from the sample inlet port to the reaction chamber and to the analysis region for a measurement of unmodified sample material, then operates the liquid flow means in a bidirectional sample flow mode to oscillate the sample material in the reaction chamber and facilitate modification by the immobilized enzyme of the constituent of material in the sample constituent. Modified sample material is then introduced into the analysis region and the measuring system is operated to obtain a measurement of modified sample material, the measurements of modified and unmodified sample material being used to provide an indication of the amount, of the constituent of interest in the sample material, the first measurement preferably being effectively subtracted from the second measurement.

In a preferred embodiment, the liquid flow means is a positive displacement pump that is connected to a series flow path, the sample inlet port structure is connected to the inlet of the reaction chamber, the outlet of the reaction chamber is connected to the inlet of the analysis region, and the analysis region has a polarographic electrode, an ion selective electrode, and a reference electrode, and the measuring and reference electrodes are spaced from one another by a flow path portion located so that the reference electrode is downstream and spaced from the measuring electrode by a flow path volume greater than the displacement volume that sample material is moved by the pump during the bidirectional mode sample flow interval. The control means operates the pump first in the unidirectional sample flow mode to rapidly flow (at a rate of at least about one hundred microliters per second) a sample of material to be analyzed from the sample inlet port through the reaction chamber to the analysis region for a measurement of unmodified sample material, then in the bidirectional sample flow mode to oscillate the sample material in the reaction chamber and analysis region, and then again operates the pump in the unidirectional sample flow mode to flow the sample from the reaction chamber to the analysis region for a measurement of modified sample material.

In a particular embodiment, the reaction chamber has a volume of about two hundred microliters and is in the form of an elongated tube (about twenty five centimeters long) that is disposed in coil or serpentine form on a temperature stabilizing member; glucose oxidase and urease enzymes are coimmobilized on the inner surface of the tube; the polarographic electrode senses oxygen and the ion selective electrode includes nonactin ionophore for sensing ammonium ions. Flow path sections that are about three centimeters long connect the reaction chamber tube to the oxygen sensing electrode and similarly connect the ammonium sensing and reference electrodes. The analysis portions of the oxygen sensing, ammonium sensing and reference electrodes and the reaction chamber tube are housed in a temperature controlled environment that is maintained at an elevated temperature such as about 33° C.

In accordance with another aspect of the invention, there is provided a method of measuring a substance capable of being enzymatically modified that includes the steps of providing a reaction chamber that contains an immobilized enzyme capable of modifying a substance of interest, providing an analysis region spaced from the reaction chamber that includes detecting means, exposing sample material to the detecting means before the enzyme has modified the substance and providing a first output as a function of the sensed unmodified sample material, exposing the sample material to the enzyme to modify the substance of interest, then exposing the modified sample material to the detecting means and producing a second output as a function of the quantity of a constituent in the modified sample material, and processing the first and second outputs to provide an indication of the amount of the substance of interest in the sample.

In a particular embodiment, there is provided a method of measuring urea that is capable of being enzymatically converted to ammonium ions with compensation for potassium ion interference that includes the steps of contacting the sample with an ammonium ion detecting electrode before the enzyme has converted the urea to ammonium ions and measuring the output of the ion detecting electrode to provide an indication of the potassium ion interference of the sample; contacting the sample with the ion detecting electrode after the enzyme has converted urea to ammonium ions and measuring the output of the ion detecting electrode to determine the apparent amount of urea in the sample; and effectively subtracting the potassium ion interference output from the apparent urea output to determine the amount of the urea in the sample. The method preferably further comprises the step of calibrating the detecting means using first and second calibrators having known concentrations of potassium ions and urea by contacting the first and second calibrators individually with the detecting means and measuring the output of the detecting means before and after the enzyme has converted the urea in the calibrators to ammonium ions.

In accordance with another aspect of the invention, there is provided an analysis system for measuring the plurality of parameters of a fluid sample that includes a housing structure, and a flow through cell in the housing in which an inlet port, an outlet port, and at least two sensor accepting ports are defined. Structure in the cell defines a sample flow path through the flow through cell that is disposed in a generally vertical plane and that serially connects the inlet port, the sensor ports and the outlet port, and that includes a first serpentine flow path portion between the inlet port and a first sensor port and a second serpentine portion between the last sensor port and the outlet port. The serpentine portions provide isolation for the sensor ports. Preferably, the flow through cell is of transparent material such that fluid sample in said flow path may be visually observed.

In preferred embodiments, each serpentine flow path portion includes a downwardly curved portion and an upwardly curved portion, with an intervening vertical transition section. In a particular embodiment, each downwardly curved and upwardly curved portion is of about 180° extent and extends along an arc of less than one centimeter diameter and the vertical transition section is less than one centimeter long. Further, the sample flow path includes a first section that extends generally upwardly from the first serpentine flow path portion to a first sensing cavity, a second section that extends generally downwardly from the last sensing cavity to the second serpentine flow path portion, and an isolation portion that extends from the first section to the second section and is inclined generally downwardly to provide an isolation section between the first and second portions.

Other features and advantages of the invention will be seen as the following description of a particular embodiment progresses, in conjunction with the drawing, which is a diagram of an analysis system in accordance with the invention.

DESCRIPTION OF PARTICULAR EMBODIMENT

The biological fluid analysis system shown in the drawing includes sample station 10 that is connected to mixing station 12 by conduit 14, and diluent reservoir 16 that is connected to mixing station 12 by conduit 18. In a particular embodiment, mixing station 12 employs a fluidic module of the type shown in Webster U.S Pat. Nos 4,304,257 and 4,601,881, the disclosures of which are specifically incorporated herein by reference. That module employs an array of valves and one or more metering chambers and is incorporated in a clinical analyzer embodiment of the type shown in U.S. Pat No. 4,906,432 entitled LIQUID HANDLING filed concurrently herewith, the disclosure of which is specifically incorporated by reference. Such a fluidic module can be used in place of the spin cup assembly employed in the embodiment described below.

Spin cup assembly 20 at station 12 includes funnel shaped spin cup 22 that is driven by reversible DC motor 24 located beneath the assembly Diluent is flowed from reservoir 16 through tube 18 into spin cup 22 and sample is flowed from sample cup 10 through tube 14 into spin cup 22. Aspirator tube 26 is connected to inlet 28 of analysis unit 30.

Analysis unit 30 has a housing 32 in which heater structure (diagrammatically indicated at 34) is disposed, the heater being controlled to maintain a temperature of about 33° C. in housing 32. Also disposed within housing 32 is sensor module 36 that is fabricated from a clear, colorless (acrylic) material in which is formed a series flow path that extends from inlet port 80 through serpentine isolation loop 38 along a generally vertical path to analysis electrode port 42 to which oxygen sensing electrode 44 is coupled; then via flow path section 46 to analysis port 48 to which nonactin ionophore ammonium sensing electrode 50 is coupled; then via coupling flow path section 52 that extends from analysis port 48 to reference port 54 to which reference electrode is coupled, flow path section 52 including downwardly inclined (at an angle of about 30°) isolation portion 58 that is about three centimeters long, and has a volume of about twenty microliters; and from port 54 through serpentine isolation loop section 60 to module outlet port 82. Each serpentine isolation loop section includes a downwardly curved portion 84 and an upwardly curved portion 86, each of about 180° extent along an arc of about 0.4 centimeter diameter and connected by a vertical transition section of about 0.5 centimeter length.

Sensor module 36 is fabricated from a clear colorless (acrylic) polymeric material and has a width of about seven centimeters, a height of about ten centimeters, and a thickness of about one centimeter. The flow passages are of about 0.8 millimeter in diameter and are formed within module 36 at a distance of about 0.3 centimeter from its front face. Module 36 is mounted in a generally vertical plane so that the flow path sections from the serpentine isolation portion 38 past the sensor ports 42 and 48 extend generally vertically upward, and the flow path section from sensor port 54 extends generally vertically downward.

Also disposed within housing 32 is aluminum temperature stabilizing cylinder 90 on which is disposed in coil form reaction chamber tube 92 that is about 25 centimeters long and has a capacity of about 150 microliters. Urease and glucose oxidase enzymes are coimmobilized on its inner surface One end of tube 92 is connected to housing inlet 28 and its other end is connected to module inlet 80. The flow path extends from port 82 to housing outlet 62 and continues to peristaltic (or piston) pump 64. The outlet of pump 64 is connected by line 66 to waste container 68. The outputs of oxygen electrode assembly 44, ammonium electrode assemby 50 and reference electrode assembly 56 are applied via high impedance operational amplifiers 70 to control unit 72 for analogical interpretation and calculation of the activity and concentrations of ammonium ion and oxygen in the sample and transfer of resulting data to output device 74. An operator control (in the form of keyboard 76) is also coupled to controller 72.

In system operation, specified volumes of sample to be analyzed and diluent are transferred into mixing chamber spin cup 22. Controller 72 generates signals over line 94 to operate motor 24 to drive spin cup 22 in slow speed agitation to mix sample and diluent. After mixing, peristaltic pump 64 is operated in a fast flow mode (in response to controller signals on line 96) to pull diluted sample from cup 22 through aspirator tube 26 and reaction chamber coil 92 into the analysis and reference regions of electrodes 44, 50 and 56 at a flow rate of about 200 microliters per second In this condition, a first portion of the diluted sample is in contact with the ammonium, oxygen and reference electrodes 44, 50, 56 while the reaction chamber coil 92 is filled with a second portion of the diluted sample, and that portion is in contact with the coimmobilized urease and glucose oxidase enzymes because of the rapid flow through the reaction cell 92, the first portion contacting the electrodes 44, 50, 56 contains unconverted sample that has not been acted upon by the enzymes to convert urea to ammonium ions and to convert glucose to hydrogen peroxide.

Pump 64 is then operated in bidirectional mode (in response to controller signals on line 98) (alternate clockwise and counterclockwise directions of rotation) to oscillate the diluted sample portions in the analysis regions and the reaction chamber 92 back and forth over a distance of about one centimeter. This bidirectional flow mode promotes enzyme-sample contact within reaction chamber 92 and equilibration at electrodes 44, 50, 56. The bidirectional mode operation of pump is then terminated and the output from the electrodes 44, 50, 56 (in millivolts for ammonium electrode 44 and in picoamperes for oxygen electrode 50) is recorded by controller 72 to provide first data values (unconverted or pre enzymatic reaction sample data—that is, data before urea in the sample has been converted to ammonium ions and glucose has been converted to hydrogen peroxide).

Following acquisition of these first data values, and after glucose and oxygen in the second diluted sample portion has reacted with the immobilized glucose oxidase enzyme to form gluconic acid and hydrogen peroxide and urea in the second diluted sample portion has reacted with the immobilized urease enzyme to form ammonium ions and carbon dioxide, pump 64 is operated in unidirectional flow mode (line 96) to pull the second diluted sample portion from reaction chamber 92 into the analysis regions of electrodes 44, 50 and 56. Pump 64 is again operated in bidirectional flow mode (line 98) to oscilliate the sample portion in alternate directions to promote electrode equilibration. After that equilibration interval, a second set of data readings are taken, that data representing the apparent ammonium concentration in the converted sample mixture.

After the second set of data is collected, pump 64 is operated in unidirectional flow mode to discard the sample to waste 68 and the flow path is washed with buffer solution. The two sets of data provide 1) pre-enzymatic reaction (background) measurements representing interfering (primarily potassium ion in the case of electrode 50) contribution to the electrode response; and 2) post enzymatic reaction measurements (representing apparent ammonium concentration—response to both ammonium and interfering ion contributions—in the case of electrode 50).

The actual concentration of glucose in the sample is determined by effectively subtracting pre-enzymatic reaction data from post enzymatic reaction data. Similarly, the actual concentration of urea in the sample is determined by effectively subtracting pre-enzymatic reaction data from post enzymatic reaction data using the following form of the Nicolsky equation:

$$\text{conc.}_{UN} = \text{antilog}\ [(E_S E_{cal\ 1})(1/S)] * (\text{Cal}\ 1_{UN} + k\text{Cal}_{1k}) - (k\ \text{conc.}\ K) \quad (1)$$

where

Conc.$_{UN}$ = actual concentration of urea in the sample;

$E_s$ = post-enzymatic reaction measurement for the sample in millivolts;

$E_{cal1}$ = post enzymatic reaction measurement for calibrator 1 in millivolts;

Cal$1_{UN}$ = actual concentration of urea in calibrator 1 (known);

Cal$_{1k}$ = actual concentration of potassium in calibrator 1 (known);

k = potassium selectivity factor for the electrode; conc. K = concentration of potassium in the sample.

The selectivity factor k is determined experimentally for electrode 50 using calibrators having known concentrations of urea and potassium ions, and for this electrode is approximately 1/5, meaning that about five potassium ions in the sample are counted as one ammonium ion by the electrode.

The slope S is theoretically a constant equal to RT/ZF, where R is the universal gas constant, T is the temperature, Z is the ionic charge of the ion produced, and F is Faraday's constant In practice, however, the value of S is determined from the calibration data according to the following equation:

$$S = WE_F/\log \frac{Cal\ 1_{UN} + kCal\ 1_k}{Cal\ 2_{UN} + kCal\ 2_k} \quad (2)$$

where k, Cal $1_{UN}$, and Cal $1_k$ are as defined in equation (1);

Cal $2_N$ = actual concentration of urea in calibrator 2 (known);

Cal $2_k$ = actual concentration of potassium in calibrator 2 (known);

W $E_F$ = difference in millivolts between the post enzymatic reaction measurements for calibrators 1 and 2.

The concentration of potassium in the sample (conc. K) is determined from the pre enzymatic reaction data obtained from the two calibrators and the sample using the Nicolsky equation. Because urea is not converted to ammonium ions during the pre-enzymatic reaction cycle, the Nicolsky equation reduces to the following form:

$$\text{conc.}\ K = \text{antilog}\ \frac{WE_B}{S^1} * Cal\ 1_k \quad (3)$$

where

Cal $1_k$ is as defined in equation (1);

$WE_B$ = difference in millivolts between the calibrator 1; and $S^1$, like slope S, is theoretically a constant, but in practice is determined experimentally from the pre-enzymatic reaction calibration data according to the following equation:

$$S^1 = WE_B/\log \frac{Cal\ 1_k}{Cal\ 2_k} \quad (4)$$

where

Cal $1_k$ and Cal $2_k$ are as defined in equation 2;

$WE_B$ = difference in millivolts between the pre enzymatic reaction measurements of calibrators 1 and 2.

Thus, by using equations 1-4, and obtaining pre-enzymatic reaction measurements for the two calibrators and sample, and post enzymatic reaction measurements for the two calibrators and sample, the actual urea concentration in the sample is obtained.

In a specific example, 12 microliters of sample and 450 microliters of a buffered calibration solution (Tris-HCl buffer, pH 7.5) having a potassium ion concentration of 8 millimols per liter and a urea concentration of 50 milligrams per deciliter were placed in mixing station 12. After mixing, the diluted solution was then pulled from station 12 into reaction coil 92 and the analysis and reference regions of electrodes 44, 56 at a rate of about 190 microliters per second using positive displacement pump 64. Pump 64 then was operated to produce back and forth (oscillating) flow of the calibration solution for thirteen seconds after which a pre enzymatic reaction measurement (ten data points taken at 100 millisecond intervals) was taken at electrodes 50, 56. After pre-enzymatic reaction data had been collected, the calibration solution was pulled from the reaction coil 92 and positioned in the analysis and reference regions of electrodes 50, 56 at a rate of about 190 microliters per second, and pump 64 was again operated to oscillate the calibration solution for about eight seconds. A second set of ten measurements, representing post-enzymatic reaction data, was then taken. After collection of this data, the first calibration solution was removed and the flow path washed for about nine seconds with Tris HCl buffer solution to remove traces of the calibrator solution.

Following the buffer rinse, the procedure was repeated with a second buffered calibration solution having a potassium ion concentration of 2 millimols per liter and a urea concentration of 20 milligrams per deciliter to obtain pre enzymatic reaction and post-enzymatic reaction data on the second calibration solution.

A twelve microliter volume of serum sample diluted with 450 microliters of Tris-HCl buffer (0.05 M, pH 7.5+0.01) was then placed in mixing station 12 and similarly flowed through the reaction chamber 92 and analysis and reference regions of electrodes 50, 56 and pre-enzymatic (background) and post enzymatic reaction data similarly collected At the end of the data collection, the data was analyzed to obtain the actual urea concentration of the serum sample in accordance with the above data analysis procedure.

While a particular embodiment of the invention has been shown and described, various modifications will be apparent to those skilled in the art, and therefore it is not intended that the invention be limited to the disclosed embodiment, or to details thereof, and departures may be made therefrom within the spirit and scope of the invention.

What is claimed is:

1. A method for measuring a constituent of interest of a biological fluid or the like comprising the steps of
   providing a reaction chamber that contains an immobilized enzyme capable of modifying a constituent of interest,
   providing a measuring system,
   placing a first portion of a biological fluid to be analyzed in said reaction chamber and concurrently exposing a second unmodified portion of said biological fluid to said measuring system to provide a first data output,
   oscillating said first biological fluid portion with bidirectional flow in said reaction chamber to facilitate modification by said immobilized enzyme of said constituent of interest in said biological fluid,
   then exposing said first portion of said biological fluid to be analyzed to said measuring system to provide a second data output, and
   modifying said second data output as a function of said first data output to provide an indication of the actual amount of said constituent of interest in said biological fluid.

2. The method of claim 1 wherein said measuring system includes an analysis region and said analysis region and said reaction chamber are connected together in a series flow path, and
   said first and second portions of said biological fluid are placed in said reaction chamber and exposed to said measuring system by flowing said biological fluid to be analyzed through said reaction chamber at a flow rate of at least about one hundred microliters per second.

3. The method of claim 1 wherein said constituents of interest are urea and glucose, and two different enzymes are coimmobilized in said reaction chamber.

4. The method of claim 3 wherein said two different coimmobilized enzymes are glucose oxidase and urease and said measuring system includes an ammonium ion selective electrode and an oxygen sensing electrode.

5. A method of measuring a substance capable of being enzymatically converted to a detectable ion with compensation for potassium ion interference comprising the steps of
   placing a sample containing a substance capable of being enzymatically converted to a detectable ion in a chamber comprising an immobilized enzyme capable of converting said substance to said detectable ion and detecting means for detecting said detectable ion;
   contacting said sample with said detecting means before said immobilized enzyme has converted said substance to said detectable ion and measuring the output of said detecting means to provide a potassium ion interference (pre-enzymatic reaction) output;
   oscillating said sample in said chamber in a bidirectional flow mode interval to facilitate conversion by said immobilized enzyme of said substance in said sample to said detectable ion;
   contacting said sample with said detecting means after said immobilized enzyme has converted said substance to said detectable ion and measuring the output of said detecting means to provide an apparent substance amount output; and
   modifying said post-enzymatic reaction output as a function of said pre-enzymatic reaction output to provide an indication of the actual amount of a substance in said sample using a form of the Nicolsky equation.

6. The method of claim 5 wherein said substance comprises urea and said detectable ion comprises ammonium ion.

7. The method of claim 5 wherein said detecting means comprises an ion selective electrode and a reference electrode, said ion selective and reference 8. A method of measuring a substance capable of being enzymatically converted to a detectable ion with compensation for potassium ion interference comprising the steps of
   placing a sample containing a substance capable of being enzymatically converted to a detectable ion in a chamber comprising an immobilized enzyme capable of converting said substance to said detectable ion and detecting means for detecting said detectable ion;

contacting said sample with said detecting means before said immobilized enzyme has converted said substance to said detectable ion and measuring the output of said detecting means to provide a potassium ion interference (pre-enzymatic reaction) output;

oscillating said sample in said chamber with bidirectional flow to facilitate conversion by said immobilized enzyme of said constituent of interest in said sample to said detectable ion;

contacting said sample with said detecting means after said enzyme has converted said substance to said detectable ion and measuring the output of said detecting means to provide an apparent substance amount (post-enzymatic reaction) output; and modifying said post-enzymatic reaction output as a function of said pre-enzymatic reaction output to provide an indication of the actual amount of a substance in said sample. electrodes are spaced from one another by a flow path portion located so that said reference electrode is downstream of and spaced from said ion selective electrode by a flow path volume greater than the displacement volume that sample material is moved during said bidirectional sample flow mode interval.

9. The method of claim 8 further comprising the step of calibrating said detecting means using first and second calibrators having known concentrations of potassium ions and said substance by contacting said first and second calibrators individually with said detecting means and measuring the output of said detecting means before and after said enzyme has converted said substance in said calibrators to said detectable ion.

10. The method of claim 9 wherein said substance is urea and the actual concentration of urea in said sample is determined by effectively subtracting said pre-enzymatic reaction data from said post enzymatic reaction data using the following form of equation:

$$\text{conc.}_{UN} = \text{antilog}\,[(E_S - E_{cal\,1})(1/S)] * (\text{Cal}\,1_{UN} + k\text{Cal}_{1k}) - (k\,\text{conc.}\,K)$$

where
- $\text{conc.}_{UN}$ = actual concentration of urea in the sample;
- $E_s$ = post-enzymatic reaction measurement for the sample in millivolts;
- $E_{cal1}$ = post-enzymatic reaction measurement for calibrator 1 in millivolts;
- $\text{Cal}\,1_{UN}$ = actual concentration of urea in calibrator 1 (known);
- $\text{Cal}\,1_k$ = actual concentration of potassium in calibrator 1 (known);
- $k$ = potassium selectivity factor for the electrode; and
- $\text{conc.}\,K$ = concentration of potassium in the sample.

11. The method of claim 10 wherein said ion selective electrode includes nonactin ionophore, and said immobilized enzyme includes urease enzyme.

12. The method of claim 8 that further includes the concurrent measurement of a second substance in said sample, and a second enzyme is coimmobilized in said reaction chamber.

13. The method of claim 12 wherein said detecting means and said chamber are connected together in a series flow path, and said sample to be analyzed is flowed through said chamber to said detecting means at a flow rate of at least about one hundred microliters per second.

14. The method of claim 13 wherein said second substance in said sample is glucose and said coimmobilized second enzyme is glucose oxidase.

15. The method of claim 14 wherein said ion selective electrode includes nonactin ionophore, and the other coimmobilized enzyme is urease.

* * * * *

UNITED STATES PATENT AND TRADEMARK OFFICE
CERTIFICATE OF CORRECTION

PATENT NO. : 5,158,868

DATED : October 27, 1992

INVENTOR(S) : Carolyn Bergkuist et al.

Page 1 of 3

It is certified that error appears in the above-identified patent and that said Letters Patent is hereby corrected as shown below:

On the title page:

In the References Cited (OTHER PUBLICATIONS) section:

Pacakova, Vera: "Determination" should read --Determinations--.

Column 1, line 51, after "amount" delete "," (comma).
Column 4, line 15, before "is coupled" insert --56--.
Column 4, line 43, after "surface" insert --.-- (period).
Column 4, line 67, after "second" insert --.-- (period).
Column 5, line 5, "enzymes because" should read --enzymes. Because--.
Column 5, line 24, "pre enzymatic" should read --pre-enzymatic--.
Column 5, line 52, "post enzymatic" should read --post-enzymatic--.
Column 5, lines 54-55, "contribution-s" should not be broken at end of line.
Column 5, line 58, "post enzymatic" should read --post-enzymatic--.

UNITED STATES PATENT AND TRADEMARK OFFICE
CERTIFICATE OF CORRECTION

PATENT NO. : 5,158,868

DATED : October 27, 1992

INVENTOR(S) : Carolyn Bergkuist et al.

It is certified that error appears in the above-identified patent and that said Letters Patent are hereby corrected as shown below:

Column 6, line 3, "post enzymatic" should read --post-enzymatic--.
Column 6, line 31, "Cal2$_N$" should read --Cal2$_{UN}$--.
Column 6, line 39, "pre enzymatic" should read --pre-enzymatic--.
Column 6, line 51, before "calibrator" insert --pre-enzymatic reaction measurement of the sample and--.
Column 6, lines 64-65, "pre enzymatic" should read --pre-enzymatic--.
Column 6, line 68, "post enzymatic" should read --post-enzymatic--.
Column 7, line 14, "pre enzymatic" should read --pre-enzymatic--.
Column 7, line 26, "Tris HCl" should read --Tris-HCl--.
Column 7, line 34, "pre enzymatic" should read --pre-enzymatic--.
Column 7, line 41, "post enzymatic" should read --post-enzymatic--.
Column 7, line 42, after "collected" insert --.-- (period).

UNITED STATES PATENT AND TRADEMARK OFFICE
CERTIFICATE OF CORRECTION

PATENT NO.   : 5,158,868

DATED        : October 27, 1992

INVENTOR(S)  : Carolyn Bergkuist et al.

It is certified that error appears in the above-identified patent and that said Letters Patent are hereby corrected as shown below:

Column 8, line 60, claim 7, after "reference" insert --electrodes are spaced from one another by a flow path portion located so that said reference electrode is downstream of and spaced from said ion selective electrode by a flow path volume greater than the displacement volume that sample material is moved during said bidirectional sample flow mode interval.--

Column 9, line 21, claim 8, delete "electrodes are spaced".

Column 9, claim 8, delete lines 22-27 ("from . . . interval.").

Column 10, line 1, "post enzymatic" should read --post-enzymatic--.

Signed and Sealed this

Twelfth Day of October, 1993

Attest:

Attesting Officer

BRUCE LEHMAN

Commissioner of Patents and Trademarks